(12) United States Patent
Lin (10) Patent No.: US 11,286,505 B2
(45) Date of Patent: *Mar. 29, 2022

(54) METHOD TO PRODUCE PROTEIN IN ASPERGILLUS NIGER'S RESTING SPORES USING SSRNA

(71) Applicant: FUZHOU UNIVERSITY, Fuzhou (CN)

(72) Inventor: Jun Lin, Fuzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/296,267

(22) Filed: Mar. 8, 2019

(65) Prior Publication Data

US 2019/0276853 A1 Sep. 12, 2019

Related U.S. Application Data

(63) Continuation of application No. PCT/CN2016/102925, filed on Oct. 21, 2016.

(30) Foreign Application Priority Data

Sep. 9, 2016 (CN) .......................... 201610812864.2

(51) Int. Cl.
| | |
|---|---|
| *C12N 13/00* | (2006.01) |
| *C12N 15/90* | (2006.01) |
| *C12N 1/14* | (2006.01) |
| *C12N 15/87* | (2006.01) |
| *C12R 1/685* | (2006.01) |

(52) U.S. Cl.
CPC ............... *C12N 15/90* (2013.01); *C12N 1/14* (2013.01); *C12N 13/00* (2013.01); *C12N 15/87* (2013.01); *C12N 1/145* (2021.05); *C12R 2001/685* (2021.05)

(58) Field of Classification Search
CPC .......... C12N 15/90; C12N 15/87; C12N 1/14; C12N 1/145; C12N 13/00; C12R 2001/685
See application file for complete search history.

(56) References Cited

U.S. PATENT DOCUMENTS

| | | | |
|---|---|---|---|
| 2009/0260102 A1 | 10/2009 | Kuo | |
| 2010/0304468 A1* | 12/2010 | Kim ....................... | C12N 15/87 435/254.6 |

OTHER PUBLICATIONS

Bapat, Prashant ., An Optimized Method for Aspergillus niger Spore Production on Natural Carrier Substrates. Biotechnol. Prog. 2003, 19, 1683-1688 (Year: 2003).*
Wu, Mengxi et al., High-density distributed electrode network, a multi-functional electroporation method for delivery of molecules of different sizes, Scientific Reports vol. 3, Article No. 3370 (2013). (Year: 2013).*
Ababutain, Ibtisam Mohammed, Effect of Some Ecological Factors on The growth of Aspergillus niger and Cladosporium sphaerospermum. American Journal of Applied Sciences, 10 (2): 159-163, 2013. (Year: 2010).*
Potter, Huntington., Heller, Richard,. Transfection by Electroporation. Current Protocols in Cell Biology 20.5.1-20.5.10, Sep. 2011 (Year: 2011).*
Reberšek, Matej., Miklavcic, Damijan. Concepts of Electroporation Pulse Generation and Overview of Electric Pulse Generators for Cell and Tissue Electroporation. Concepts of Electroporation Pulse Generation and Overview, 2010; pp. 323-339. (Year: 2010).*
Ozeki et al., Transformation of Intact Aspergillus niger by Electroporation, 1994, Biosci. Biotech. Biochem, vol. 58, pp. 2224-2227 (Year: 1994).*
Thermo Scientific. 2012. "MAN0013096_RiboRuler_HighRange_ RNA_Ladder_UG" #SM1821. https://assets.thermofisher.com/TFS-Assets/LSG/manuals/MAN0013096_RiboRuler_HighRange_RNA_ Ladder_UG.pdf (Year: 2012).*
Internation Search Report of PCT/CN2016/102925, dated Jun. 12, 2017.
Wu. et al. High-density distributed electrode network, a multi-functional electroporation method for delivery of molecules of different sizes. Scientific Reports vol. 3, Article No. 3370 (2013).

* cited by examiner

*Primary Examiner* — Antonio Galisteo Gonzalez
*Assistant Examiner* — Khaleda B Hasan
(74) *Attorney, Agent, or Firm* — W&KIP (57) ABSTRACT

A method to produce protein in *Aspergillus niger*'s sleeping spores using single-stranded RNA is provided. The method includes three steps: culture of *Aspergillus niger* and collection of spores, pretreatment of *Aspergillus niger* spores, and electroporation of *Aspergillus niger* spores using HDEN method. Non-germinated spores are used as a starting material for introduction of exogenous molecules. The exogenous protein coding single-stranded RNA is introduced into the resting spores of *Aspergillus niger* by employing the HDEN electrotransformation technique to express protein. This method is simple and fast, the effect is excellent, and the transformation rate reaches more than 90%.

6 Claims, 4 Drawing Sheets
Specification includes a Sequence Listing.

SEQUENCE LISTING

<160> NUMBER OF SEQ ID NOS: 10

<210> SEQ ID NO 1
<211> LENGTH: 31
<212> TYPE: DNA
<213> ORGANISM: Artificial Sequence
<220> FEATURE:
<223> OTHER INFORMATION: Synthesized

<400> SEQUENCE: 1
agatgacgtc gctagcatgg tgagcaaggg c    31

<210> SEQ ID NO 2
<211> LENGTH: 27
<212> TYPE: DNA
<213> ORGANISM: Artificial Sequence
<220> FEATURE:
<223> OTHER INFORMATION: Synthesized

<400> SEQUENCE: 2
acgcgtcgac ttacttgtac agctcgt    27

<210> SEQ ID NO 3
<211> LENGTH: 34
<212> TYPE: DNA
<213> ORGANISM: Artificial Sequence
<220> FEATURE:
<223> OTHER INFORMATION: Synthesized

<400> SEQUENCE: 3
cggaattcgc caccatggcc tcctccgagg acgt    34

<210> SEQ ID NO 4
<211> LENGTH: 28
<212> TYPE: DNA
<213> ORGANISM: Artificial Sequence
<220> FEATURE:
<223> OTHER INFORMATION: Synthesized

<400> SEQUENCE: 4
tcgagctcgt taggcgccgg tggagtgg    28

<210> SEQ ID NO 5
<211> LENGTH: 720
<212> TYPE: DNA
<213> ORGANISM: Artificial Sequence
<220> FEATURE:
<223> OTHER INFORMATION: Synthesized

<400> SEQUENCE: 5
atggtgagca agggcgagga gctgttcacc ggggtggtgc ccatcctggt cgagctggac    60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420

```
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 6
<211> LENGTH: 239
<212> TYPE: PRT
<213> ORGANISM: Artificial Sequence
<220> FEATURE:
<223> OTHER INFORMATION: Synthesized

<400> SEQUENCE: 6

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 7
<211> LENGTH: 678
<212> TYPE: DNA
<213> ORGANISM: Artificial Sequence
<220> FEATURE:
<223> OTHER INFORMATION: Synthesized

<400> SEQUENCE: 7

```
atggcctcct ccgaggacgt catcaaggag ttcatgcgct tcaaggtgcg catggagggc    60
tccgtgaacg gccacgagtt cgagatcgag ggcgagggcg agggccgccc ctacgagggc    120
```

```
acccagaccg ccaagctgaa ggtgaccaag ggcggccccc tgcccttcgc ctgggacatc    180
ctgtcccctc agttccagta cggctccaag gcctacgtga agcaccccgc cgacatcccc    240
gactacttga agctgtcctt ccccgagggc ttcaagtggg agcgcgtgat gaacttcgag    300
gacggcggcg tggtgaccgt gacccaggac tcctccctgc aggacggcga gttcatctac    360
aaggtgaagc tgcgcggcac caacttcccc tccgacggcc ccgtaatgca gaagaagacc    420
atgggctggg aggcctccac cgagcggatg taccccgagg acggcgccct gaagggcgag    480
atcaagatga ggctgaagct gaaggacggc ggccactacg acgccgaggt caagaccacc    540
tacatggcca agaagcccgt gcagctgccc ggcgcctaca agaccgacat caagctggac    600
atcacctccc acaacgagga ctacaccatc gtggaacagt acgagcgcgc cgagggccgc    660
cactccaccg cgcctaa                                                  678
```

```
<210> SEQ ID NO 8
<211> LENGTH: 225
<212> TYPE: PRT
<213> ORGANISM: Artificial Sequence
<220> FEATURE:
<223> OTHER INFORMATION: Synthesized

<400> SEQUENCE: 8

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220

Ala
225

<210> SEQ ID NO 9
<211> LENGTH: 720
```

<212> TYPE: DNA
<213> ORGANISM: Artificial Sequence
<220> FEATURE:
<223> OTHER INFORMATION: Synthesized

<400> SEQUENCE: 9

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccttcggcta cggcctgcag tgcttcgccc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagct accagtccgc cctgagcaaa gaccccaacg agaagcgcga tcacatggtc   660
ctgctggagt tcgtgaccgc cgccgggatc actctcggca tggacgagct gtacaagtga   720
```

<210> SEQ ID NO 10
<211> LENGTH: 239
<212> TYPE: PRT
<213> ORGANISM: Artificial Sequence
<220> FEATURE:
<223> OTHER INFORMATION: Synthesized

<400> SEQUENCE: 10

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205
```

```
Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

METHOD TO PRODUCE PROTEIN IN ASPERGILLUS NIGER'S RESTING SPORES USING SSRNA

CROSS-REFERENCE TO RELATED APPLICATIONS

This application is a continuation of International Patent Application No. PCT/CN2016/102925 with a filing date of Oct. 21, 2016, designating the United States, now pending, and further claims priority to Chinese Patent Application No. 201610812864.2 with a filing date of Sep. 9, 2016. The content of the aforementioned applications are incorporated herein by reference.

BACKGROUND OF THE INVENTION

1. Field of the Invention

The present invention relates to the field of biological technologies, and specifically to a method to produce protein in *Aspergillus niger*'s sleeping spores using ssRNA.

REFERENCE TO SEQUENCE LISTING

The present application contains a Sequence Listing which has been submitted in ASCII format via EFS-Web. The ASCII copy, created on May 20, 2019, is named "WK19007_ST25" and is 10,436 bytes in size. The information in the electronic format of the sequence listing is incorporated herein by reference in its entirety.

2. Description of Related Art

The central dogma of molecular biology refers to the process by which genetic information is transmitted from DNA to RNA and then from RNA to proteins, that is, to complete the transcription and translation of genetic information. In modern genetic engineering, hosts are often used to express exogenous proteins, and the common practice is to construct plasmid vectors, place encoded DNA sequences of exogenous proteins behind a strong promoter, and after importing host cells, encoded DNA sequences are transcribed into mRNA sequences (single-stranded RNA), The mRNA sequence is also expressed as a protein molecule by the translation machine in the cell to complete the whole process of exogenous protein expression.

DNA, whether as a plasmid in the cytoplasm that is outside the host genome or inserted into the host genome, can replicate itself stably and pass it on to the offspring. That is, DNA information can be inherited. At the same time, DNA can continuously transcribe newborn RNA and translate it into protein.

RNA is a growth of chain molecules by the condensation of Ribonucleic acid through the dimethyl phosphate bond. A Ribonucleic acid molecule is composed of phosphoric acid, ribose and base. There are 4 main bases of RNA, namely A (Adenine), G (Guanine), C (Cytosine), U (Uracil). RNA, as a single-stranded molecule, is unstable, has a short half-life compared to the DNA of a double-stranded structure, and in nature, RNAse are widespread and RNA is highly susceptible to degradation. RNA has the following well-known characteristics: RNA that is free in the cytoplasm is not inherited; the RNA half-life is short and cannot persist; and RNA is not inserted into the host's genomic DNA.

Because of its short half-life, the time an RNA molecule that present in the cell is also short, and the RNA can only interact with ribosomes to express protein molecules for a short period of time. The protein molecules that are expressed also have a lifespan, and how long a protein molecule exists in the cells can also be measured by half-life.

With traditional genetic engineering techniques, if exogenous proteins are to be expressed within a host cell, the common practice is to construct the encoded gene of the protein on a DNA plasmid, then transfer this DNA plasmid into the host cell, then the DNA plasmid continuously reproduces RNA, which encodes protein, and the target protein is constantly translated. The expression of protein in cells was realized by this way.

If the single-stranded RNA molecule that encodes the protein is prepared in vitro without the help of a shuttling DNA plasmid, only the exogenous single-stranded RNA encoding the protein is imported into the host cell, and as long as there is no corresponding DNA in the cell to continuously transcribe the new RNA, then the RNA produced in vitro and its expressed protein molecules, can only exist in a specific time period. In other words, this RNA and the protein molecules it expresses can only exist at some point in the cell's life.

Therefore, this feature plays an important role to realize the instantaneous expression of a protein or RNA in a specific time period, the protein can be expressed without affecting or affecting as little as possible the normal physiological cycle and genetic information of the cell. For example, at some point in cell life cycle, cells can be transferred with exogenous RNA, which may express a cytokine, regulate the life cycle of cells, and genome editing tool such as TALENs, ZFNs and CRISPR/Cas9 can be expressed using exogenous single-stranded RNA in the host cell, avoiding the use of plasmid or other forms of DNA carrier, which may lead the foreign DNA sequence introduced into the host cells, and result in the potential for the exogenous DNA interacting with the host chromosome (such as homologous recombination), affecting the heredity of host, and so on. This feature of RNA is of great value in the field of genetic engineering.

In mammalian cell experiments, there are precedents that exogenous single-stranded RNA can be transferred directly into mammalian cells. The main methods include: 1, using chemical methods such as Lipo, Lipo and other chemical reagents can interact with the cell membranes of mammalian cells, importing exogenous RNA into the cell. 2, traditional electroporation methods, such as square wave electroporation, which generates electrical pulses on the mixture of exogenous RNA and mammalian cells, making exogenous RNA into the cell.

*Aspergillus niger* is a eukaryotic microorganism and a filamentous fungus. *Aspergillus niger* is an important strain in fermentation industry, with which a variety of important industrial products such as amylase, acid protease, cellulase, pectinase, glucose oxidase, citric acid, gluconic acid and gallic acid can be produced. *Aspergillus niger* is a microbial species classified as GRAS (Generally Recognized as Safe) certified by the United States Food and Drug Administration. It is generally accepted in the field that the application of GRAS is substantially not harmful to human and the environment, and therefore, these microbial strains are able to meet a variety of increasingly stringent and harsh quality standards and can easily pass a variety of biosafety and food safety approval processes. Accordingly, the importance of *Aspergillus niger* in the modern fermentation industry is evident.

Fungal spores are the major reproductive organs of fungi, and the spores are dormant and can survive for a long time. Spores are activated and germinated under appropriate external conditions, to form mycelia for split propagation. Most importantly, the spores of many types of fungi are native haploids. Haploid can be genetically engineered directly and the efficiency is much higher than manipulating polyploids.

However, since the spores are generally dormant, their cell walls are very thick, and the state of the cell wall and cell membrane of resting spores are different from those of germinated spores and mycelia. Moreover, the intracellular life activity of resting spores is also in the least exuberant state. Therefore, it is well known in the art that resting spores have less cell permeability compared to germinated spores and mycelia. The resting spores hardly exchange substance with the exterior, and is inactive and is generally in dormant state. However, the germinated spores or mycelia, require uptake of nutrients from the exterior for life activities, so permeability of the cell wall and cell membrane is higher than the resting spores. Therefore, it is very difficult to introduce exogenous RNA molecules directly into the interior of sleeping spores. At present, there is no way to directly introduce exogenous RNA molecules into dormant (un-germinated) fungal spores without medium-mediated conditions. This is also a technical problem that has not been tackled in this field.

There have been no reports of the introduction of exogenous single-stranded RNA into *Aspergillus niger* cells, let alone the introduction of exogenous RNA into *Aspergillus niger* spores (whether germinated spores or un-germinated spores). At present, the method of expressing the target protein in *Aspergillus niger* cells by genetic engineering technology still needs to use the DNA plasmid, and generally need the protoplast of the mature mycelium of *Aspergillus niger* as the host cell, or use *Agrobacterium* as the medium to carry foreign DNA into the host cell.

In addition, when the exogenous RNA encoding protein is imported into the un-germinated spores, it is also necessary to interact with various cytokines and enzymes, such as protein translation factors inside the spores, in order to express the protein molecules. However, it is well known that the life activity of sleep spores is in the least exuberant state, the vitality of various protein translation factors and enzymes in cells is very low, the amount of various factors and enzymes is also very rare, even if exogenous RNA enters the inside of un-germinated spores, it also needs a relatively long interaction time, in order to translate the target protein. The more time means that the more probability of exogenous RNA being degraded by intracellular RNAse in the cell, so a sufficient number of exogenous RNA molecules are required to enter the inside of the un-germinated spores.

There are already ready-made technical solutions in this field to germinate fungal spores, but no matter which germination method, it takes time, energy, manual operation, and chemical reagents. There have been precedents for introduction of exogenous DNA to fungal spores. Therefore, according to the basic theory of the field, it is generally believed that the use of more cellular permeability of germinated spores to introduce exogenous molecules (such as exogenous RNA) has a greater success rate, because the germinated spores have woken up, various factors and enzymes in the cell have been fully actively, the cells desire to absorb nutrients, as well as to exchange internal and external material. Unfortunately, so far, there has been no precedent for the introduction of exogenous encoded RNA for spores (whether germinated or un-germinated). However, it is obvious that the use of un-germinated spores as a starting material for the introduction of exogenous molecules is very simple, because the complex step of spore germination can be omitted, and more importantly, the germinated spores, may have been polyploid, and the un-germinated spores, can be guaranteed to be haploid. It is required that the host cell must be haploid in order to achieve the desired result or efficiency in many genetic engineering applications. Therefore, the present invention attempts to bypass the fungal spore germination step, directly use the dormant spores, to import exogenous RNA.

In addition, fungi are known to produce a large amount of RNAse, and can secrete them outside, fungi are one of the main sources of RNA enzymes in nature. Fungal spores collected from cultures carry a large amount of RNAse, and it is difficult to thoroughly clean the RNAse without killing spores (wash with DEPC or other compounds will certainly kill fungal spores). And the spores themselves produce and secrete some RNAse. Therefore, deliver exogenous single-stranded RNA to fungal spores is very difficult, single-stranded RNA will be degraded by RNAse before into spores.

In conclusion, introducing the RNA molecules that encode proteins directly into fungi (whether mycelium or spores, whether germinated spores or un-germinated spores) are a technical problem that has not been tackled be any report in this field.

Electroporation is a method by which electrical pulses briefly act on cells that contact with exogenous nucleic acids and allow exogenous nucleic acids to enter cells. It has been reported that the use of Electroporation method to transmit DNA into *Aspergillus niger* germinated spores. However, DNA is completely different in structure, biochemistry and molecular biological properties than single-stranded RNA encoding proteins, and they interact with cell walls and cell membranes in different ways, so there are also different mechanisms for them to pass through the cell walls and cell membranes of *Aspergillus niger*. DNA molecules have long half-life, are not easily degraded, and are very stable compared to single-stranded RNA. The method used to deliver DNA cannot be used directly to deliver single-stranded RNA, and there is no relevant report.

High-density distributed electrode network (HDEN) electro-transformation technique introduced in 2013 is an electro-transformation technique developed specifically for the characteristics of mammalian cells, with the purpose of to improve the efficiency of delivery of exogenous DNA and drug to mammalian cells. The technique consists of three parts, first is the form of an electric pulse applied to cell sample, second is the solution environment where the cell sample is electroporated, and third is the culturing method of the cell sample and the pre-treatment method before electroporation. Because the technique is developed specifically for mammalian cells, the above-mentioned three parts are designed targeted for the characteristics of mammalian cells.

Application of the HDEN technique for delivery of DNA in mammalian cells such as HEK-293A, Hela, Neuro-2A, MCF-7, C2C12, 3T3-L1, CHO, MDCK, HL-60, HUVEC, A375, U251 etc. is reported in the current literatures. Currently, there are no reports on the use of this technique in species other than mammalian cells at present. Therefore, whether the HDEN electro-transformation technique can be applied to species other than mammalian cells is still unknown.

SUMMARY OF THE INVENTION

The purpose of this invention is to provide a method for expressing protein in the dormant spores of *Aspergillus* niger by using exogenous single-stranded RNA, which bypasses the step of fungal spore germination step and uses HDEN electro-transformation technology to deliver the in vitro single-stranded encoded protein RNA through the cell wall and cell membrane and express protein in the dormant spores of *Aspergillus niger*.

To achieve the above objective, the present invention employs the following technical solutions:

A method for direct transformation of exogenous protein coding single-stranded RNA into resting spores of *Aspergillus niger* including the steps of:

1) Culture of *Aspergillus niger* and Collection of Spores

*Aspergillus niger* is inoculated onto a surface of a solid agar medium, and cultured until the *Aspergillus niger* spores are overgrown on the surface of the medium, the *Aspergillus niger* spores are washed off from the surface of the medium, suspension of the spores is aspirated off and filtered to remove mycelia, and filtrate containing the spores is collected, and centrifuged to collect the pelleted resting spores;

2) Pretreatment of *Aspergillus niger* Spores the spores are re-suspended in an electroporation buffer, and centrifuged to collect the spore pellets, the re-suspension and centrifugation steps are repeated 3-4 times, and the last collected spore pellets are re-suspended in the electroporation buffer, to obtain an *Aspergillus niger* spore suspension with a spore concentration of $10^4$-$10^{11}$ spores/ml, in which the electroporation buffer consists of 4-hydroxyethyl piperazineethanesulfonic acid (HEPES) having a final concentration of 0.01-100 mmol/L and mannitol having a final concentration of 0.5-5000 mmol/L, and the pH of the electroporation buffer is 3.0-9.5;

3) Electroporation of *Aspergillus niger* Spores by Using HDEN Method

The *Aspergillus niger* spore suspension prepared in the above steps and a RNA to be transformed are added to wells of a cell culture plate and mixed uniformly, in order to obtain a mixture of the spores and the RNA, the cell culture plate is placed on an ice bath for 10-15 min, electroporation is carried out subsequently by using the HDEN method with an Etta Biotech X-Porator H1 electroporator, by inserting an electroporator head fitted with a matrix electrode into the mixture of the spores and the RNA, and then energizing, to generate an electric field inside the mixture of the spores and the RNA, the cell culture plate is placed on the ice bath again for 10-15 min after electroporation, and subsequently the mixture of the spores and the RNA is aspirated off, to obtain resting spores of *Aspergillus niger* with introduction of exogenous RNA, in which ratio of the *Aspergillus niger* suspension to the RNA to be transformed is 0.6-60000 μl of *Aspergillus niger* spore suspension to 0.1-10000 μg of RNA to be transformed; and parameters for the electroporation include: a voltage of 1-6000 V, pulse duration of 2-2000000 ms, and repeat for 1-100 times at an interval of 5-50000 ms.

Further, the medium in the step 1) is PDA medium, YPD medium or Czapek-Dox medium, and the preferable PDA medium is with the best outcome and the spore production capability is the fastest and the largest.

In the step 1), *Aspergillus niger* is at a temperature of 16-40° C. with 15-85% humidity for 3-15 days.

Preferably, in the step 1), *Aspergillus niger* is cultured at a temperature of 30° C. with 50-60% humidity for 5 days.

Further, in the step 2), the electroporation buffer consists of HEPES having a final concentration of 1-10 mmol/L and mannitol having a final concentration of 50-100 mmol/L, and the pH of the electroporation buffer was 5.0-7.0.

Preferably, in the step 2), the electroporation buffer consists of HEPES having a final concentration of 1 mmol/L and mannitol having a final concentration of 50 mmol/L, and the pH of the electroporation buffer was 7.0.

In the step 2), the *Aspergillus niger* spore suspension is observed under a microscope before electroporation, to confirm that the spore suspension is free of contamination with mycelia and the spores are non-germinated, and subsequently electroporation is carried out.

Further, in the step 3), the RNA to be transformed is exogenous protein encoding single-stranded RNA, which can be green fluorescent protein encoding RNA, red fluorescent protein encoding RNA or yellow fluorescent protein encoding RNA and so on.

The PCR primers for amplification of green fluorescent protein gene or yellow fluorescent protein gene are as follows:

```
                                        (SEQ ID NO. 1)
    F: 5' AGATGACGTCGCTAGCATGGTGAGCAAGGGC 3'.

(SEQ ID NO. 2)
    R: 5' ACGCGTCGACTTACTTGTACAGCTCGT 3'.
```

Among them, the GCTAGC sequence in the primer F near the 5' end is used to promote binding of eukaryotic initiation factor and RNA which in vitro transcribed from DNA, this sequence adjacent to the target gene's start codon ATG.

The PCR primers for amplification of red fluorescent protein gene is as follow:

```
    RFP-F:
                                        (SEQ ID NO. 3)
    5' CGGAATTCGCCACCATGGCCTCCTCCGAGGACGT 3'
    and RFP-R:
                                        (SEQ ID NO. 4)
    5' TCGAGCTCGTTAGGCGCCGGTGGAGTGG 3'.
```

Among them, the GCCACC sequence in the primer RFP-F near the 5' end is used to promote binding of eukaryotic initiation factor and RNA which in vitro transcribed from DNA, this sequence adjacent to the target gene's start codon ATG.

Preferably, in the step 3), in which ratio of the *Aspergillus niger* suspension to the RNA to be transformed is 60 μl of *Aspergillus niger* spore suspension to 10 μg of RNA to be transformed.

Further, in the step 3), the voltage is 300-1000 V, the pulse duration is 1500-20000 ms, repeat for 2-52 times at an interval of 500-5000 ms. Preferably, the voltage is 400 V, the pulse duration is 2000 ms, repeat for 3 times at an interval of 500 ms.

The electroporation is carried out by using the Etta Biotech X-Porator H1 electroporator purchased from Suzhou Etta Biotech Co., Ltd.

In the present invention, the experimental operations of collection of non-germinated spores and the subsequent electroporation process are all conducted in the laboratory at a constant temperature not higher than 23 degrees Celsius; the centrifugation steps are all 4 degrees Celsius cold centrifugation; and various kinds of liquid exposed to the non-germinating spores are all pre-cooled on ice in advance, unless otherwise indicated. The non-germinated spores are prohibited from contacting any factors and substances which are able to promote their germination (such as YEPD, etc. as a representative medium for germination), to ensure the dormancy of spores.

During the culture process of *Aspergillus niger* in the present invention, when *Aspergillus niger* spores are overgrown on the surface (where the spores appear dark brown), sterilized water was poured onto the surface of the medium, to wash the *Aspergillus niger* spores off from the surface of the medium. The spore suspension is aspirated with a pipette and filtered using sterilized lens paper (or fritted glass filter, filter paper, etc.) to remove the mycelia and retain the spores. If there is no filtration step, the spore suspension will be mixed up with mycelia, and it is unable to determine whether the transformants obtained in the subsequent steps are positive clones formed after transformation of RNA into the spores, or false positive clones formed after the transformation of RNA into the mycelia. The collected spores are subjected to chromosome staining, to observe and confirm that the chromosomes in the spores are haploid.

The water used to prepare the solid agar medium in the present invention should be MillQ-grade high-purity water or double distilled water having a resistivity of not lower than 18.2MΩ-cm used in molecular biology.

When *Aspergillus niger* spores are electroporated by using the HDEN method, the *Aspergillus niger* spore suspension and the RNA to be transformed are added at a proper ratio to the wells of a cell culture plate and mixed evenly. The cell culture plate was placed on an ice bath. For example, in a well of a 96-well cell culture plate (Nunclon Surface 96-well cell culture plate from NUNC, Cat. No. 167008), 60 μl of the *Aspergillus niger* spore suspension and no less than 10 μg of RNA are added to one well. The cell culture plate can also be a 384-well plate, a 24-well plate, a 6-well plate, or other larger or smaller containers, and subsequently the mixture system of the spore and the RNA can be enlarged or reduced according to the volume size ratio of the containers.

In the present invention, the above technical solution is employed. It is very simple to use non-germinated spores as a starting material for introducing exogenous molecules because the complicated step of germination of spores can be omitted. More importantly, polyploidy might have occurred in the germinated spores, whereas non-germinated spores are guaranteed to be haploid. In many applications of genetic engineering, the host cells have to be haploid in order to achieve the desired result or efficiency. Meanwhile, the HDEN electro-transformation technique is utilized in the present invention to introduce exogenous RNA into resting spores of *Aspergillus niger*. In the HDEN electro-transformation technique, a high-density matrix electrode that produces a highly uniform and intense electric field is used. Each cell within the electric field receives an electroporation condition which is almost exactly the same. During operation, the cells are placed in a common container, such as a cell culture plate, and followed by inserting an electroporator head with a matrix electrode into the container, and energized. In the traditional electroporation technique, a special electroporation cuvette is generally used, cells are placed between two metal plates positioned in parallel and subsequently the metal plates are electrified to form an electric field for electroporation. Therefore, the discharge modes in the two methods are completely different. In the former one, the electrode is inserted into the cell suspension and an electric field is generated within, whereas in the latter one, an electric field is generated outside of the whole cell suspension. In the former one, the electrode head is formed by many metal pins, and a voltage is generated between the pins, whereas in the latter one, only two metal plates are present, i.e. a positive electrode plate and a negative electrode plate, and a voltage is generated between the two plates. The HDEN technique also basically eliminates the cathode effect existing in the traditional electroporation technology, to avoid the generation of large amounts of hydroxide ions, so as to avoid killing the cells and improve the cell survival rate after electroporation. However, the cathode effect is difficult to be eliminated in the traditional electroporation technology. Furthermore, in traditional electroporation methods, the electroporation is performed only once. This is because if multiple electroporations are performed, the cell death rate will be increased greatly. However, in the HDEN method of the present invention, multiple electroporations may be performed, and the effects of the multiple electroporations can be superimposed without significantly increasing the cell death rate.

The HDEN electro-transformation technique is an electro-transformation technique developed specifically for the characteristics of mammalian cells, to improve the efficiency of delivery of exogenous DNA and drug to mammalian cells. It is well known in the art that the characteristics and the culturing methods of microbial cells are vastly different from those of mammalian cells. The structures of mammalian cells and microbial cells are different. Mammalian cells have no cell walls. Microbial cells (such as most fungi, including *Aspergillus niger*) have cell walls. The cell membrane of mammalian cells is also different from the cell membrane of microbial cells. Even in the same organism, the structures, states, and chemical compositions of respective cell membrane and cell wall of different tissues, different organs or different cell types are also different. Even the structures, states, and chemical compositions of respective cell membrane and cell wall of the same tissue, the same organ, and the same cell type of the same organism are also different in different stages of growth and development or in different external environments. The cell wall and cell membrane are barriers that block exogenous molecules to enter the cell. Depending on different barriers (with different structures and different chemical compositions), the methods to break through the barriers are different. In addition, the methods for different exogenous molecules breaking through the barrier are also different due to that different exogenous molecules with various structures, molecular weights, volumes and chemical compositions encountering the same barrier. While encountering with different barriers, the methods and mechanisms of different exogenous molecules breaking through the different barriers are even vastly different.

Therefore, any technique applied to mammalian cells is difficult to be applied directly to microbial cells. There are no reports of the use of HDEN technique in species other than mammalian cells at present. In the present invention, the exogenous protein coding RNA is introduced into resting spores of *Aspergillus niger* by using the HDEN technique according to the characteristics of *Aspergillus niger* cells. In this invention, the culture method of the cell sample, the pre-treatment method before electroporation, the solution environment of the cell sample during the electroporation, and the form of an electric pulse applied on the cell sample are determined.

In addition, in order to translate RNA into protein that require regulatory sequences to bind to eukaryotic initiation factor and mediate the initiation of protein translation. What regulatory sequences can be used in fungi (such as the *Aspergillus niger* of the present invention) is an open question that has not been reported in any literature. The invention also discloses 2 regulatory sequences which can work well in *Aspergillus niger* cells, as shown in the DESCRIPTION OF THE EMBODIMENTS of the present invention.

By using the method of the present invention, the RNA of encoded protein is introduced directly into the dormant spores of *Aspergillus niger* and the protein is expressed for the first time in history, and the steps are very simple and fast, in addition, the effect is excellent, and the transformation rate of at least 90% can be obtained.

BRIEF DESCRIPTION OF THE DRAWINGS

The following are further instructions of this invention with attached figures and DESCRIPTION OF THE EMBODIMENTS.

DESCRIPTION OF THE EMBODIMENTS

The following examples are provided for a better understanding of the present invention; however, the present invention is not limited thereto.

All the experimental process should follow the principle of aseptic condition while conducting the microbial experiments, and the instruments, consumable materials, and reagents should be sterilized.

All restriction endonuclease used in the present invention are FastDigest series obtained from Fermentas company, as well as T4 DNA ligase. Enzyme digestion and ligation and gel recovery and DNA purification, are operated in accordance with the manual from toolkit's manufacturer.

Example 1

Expression of green fluorescent protein (GFP) in *Aspergillus niger* cells:

1. Construction of Plasmid for In Vitro Transcription

The GFP gene encoding sequence is shown in SEQ ID No. 5,

The GFP protein sequence is shown in SEQ ID No. 6,

PCR primers for amplification of GFP gene:

```
F: 5' AGATGACGTCGCTAGCATGGTGAGCAAGGGC 3',

GACGTC is Aat II site.

R: 5' ACGCGTCGACTTACTTGTACAGCTCGT 3',

GTCGAC is Sal I site.
```

Among them, the GCTAGC sequence in the primer F near the 5' end is used to promote binding of eukaryotic translation initiation factor and RNA which transcribed from DNA in vitro, this sequence adjacent to the target gene's start codon ATG. After PCR with above primers, the GFP gene can be fused with GCTAGC in the upstream, and restriction enzyme cutting sites in the upstream and downstream.

PCR system (50 µl): GFP template 1 µL, primer F 2 µL, primer R 2 µL, 2×Taq PCR mix 25 µL, and ddH$_2$O top up to 50 µL. PCR program: 94° C. for 2 min, 30 cycles of (94° C. for 30 s, 61.6° C. for 30 s, and 72° C. for 60 s), and 72° C. for 5 min.

After detection of the correct PCR product by agarose gel electrophoresis, the PCR product was recovered and purified using Thermo GeneJet Gel extraction and DNA Cleanup Micro Kit.

The PCR product was cut with Aat II and Sal I, then the T4 DNA ligase was used to connect it to Promega pGEM-T easy plasmid, which was also treated by Aat II and Sal I. The ligation mix was transmitted to *Escherichia coli* with Chemical Transformation, screening for positive clones. The recombinant plasmid was extracted in large quantities after the insertion sequence was verified by sequencing. The above steps just allow the GFP gene to be located downstream of the plasmid's T7 promoter.

In Vitro Transcription:

Fermentas Company's Fastdigest Nde1 enzyme was used to linearize the recombinant plasmid. Then it was transcribed in vitro using Thermo Scientific transcriptAid T7 High Yield transcription Kit, which was operated in accordance with the manual.

Purification of Transcribed RNA Products:

1) Add 115 µl DEPC-H$_2$O and 15 µl 3M NaAc solution (pH 5.2) to the 20 µl transcription reaction system and mix evenly;

2) Add the same volume of phenol, chloroform, isoamyl alcohol mixture (phenol:Chloroform:Isoamyl alcohol=25:24:1), mix evenly;

3) High-speed centrifugation to stratify the liquid, take the upper aqueous phase to another 1.5 ml centrifugal tube.

4) Add two volume of ethanol in the aqueous phase, place at least 30 min at −20℃, centrifuge at high speed to precipitate RNA, and discard the supernatant.

5) Add 1 ml pre-cooled 70% ethanol, gently inverted the tube and then centrifuge at a high speed for 1 min.

6) The precipitation is suspended in a suitable volume of DEPC-H$_2$O, so that the RNA concentration is not less than 10 µg/µl.

Figure 1:
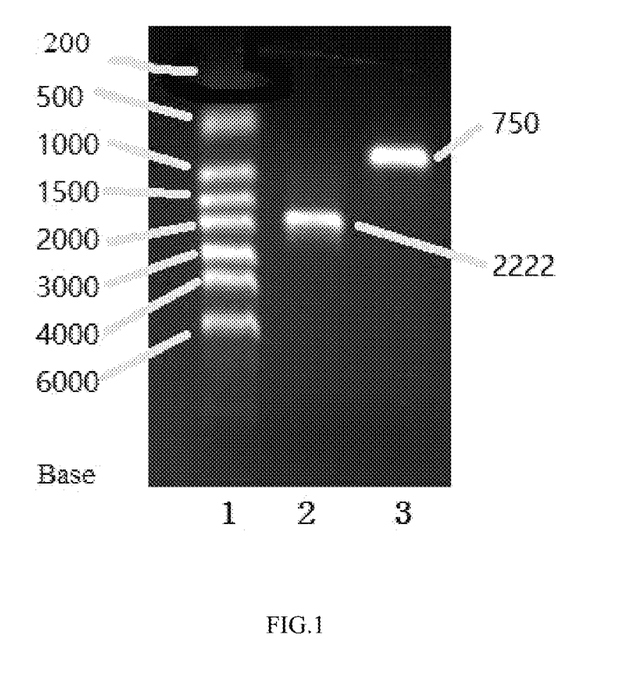
FIG. 1 is an agarose gel electrophoresis of in vitro transcribed RNA products in Example 1.

The gel electrophoresis is shown in FIG. 1:

Lane 1: RiboRuler RNA Ladder, high range, ready-to-use.

Lane 2: Positive control, 2222 nt.

Lane 3: The RNA of GFP from in vitro transcription, ~750 nt.

2. Using the above-mentioned green fluorescent protein encoded RNA to express green fluorescent protein in *Aspergillus niger* dormant spores, the steps are as follows:

1) Culture of *Aspergillus niger* and Collection of Spores

In a 15-cm Petri dish, a solid agar medium (PDA medium) was prepared. *Aspergillus niger* CBS 513.88 was inoculated onto the surface of the solid agar medium and cultured at a temperature of 30° C. with 50-60% humidity for 5 days, to allow *Aspergillus niger* spores to overgrow on the surface of the medium (where the spores appeared dark brown and was easy to visually identified).

Sterilized water was poured onto the surface of the medium, to wash down the *Aspergillus niger* spores off from the surface of the medium (by vibrating, or gently scratching with a sterilized smooth glass spreading rod). The spore suspension was aspirated with a pipette and filtered using sterilized lens paper (or fritted glass filter, filter paper, etc.) to remove the mycelia and retain the spores. The filtered liquid was placed in a centrifuge tube and centrifuged to collect the pelleted resting spores, and the supernatant was discarded. The collected spores were subjected to chromosome staining, to observe and confirm that the chromosomes in the spores are haploid.

2) Pretreatment of *Aspergillus niger* Spores

The spore pellets were re-suspended in an electroporation buffer (where the volume of the electroporation buffer added should fill up the centrifuge tube), centrifuged again to collect the spore pellets, and the supernatant was discarded. After repeating the above steps twice, the spores were re-suspended in the electroporation buffer again, and observed under a microscope, to confirm that the spore suspension was free of contamination with mycelia and the spores were non-germinated. When the spores were finally re-suspended in the electroporation buffer, the volume of the electroporation buffer was controlled to maintain a spore concentration in the *Aspergillus niger* spore suspension of $10^8$ spores/ml.

The electroporation buffer consisted of HEPES having a final concentration of 1 mmol/L and mannitol having a final concentration of 50 mmol/L, and the pH of the electroporation buffer was 7.0.

3) Electroporation of the *Aspergillus niger* Spores by Using HDEN Method

60 µl of the *Aspergillus niger* spores suspension and 10 µg of GFP protein encoding RNA were added to one well of a 96-well cell culture plate and mixed evenly, to obtain a mixture of the spores and RNA. The cell culture plate was placed on an ice bath for 10 min, electroporation was carried out subsequently by using the HDEN method using an Etta Biotech X-Porator H1 electroporator, by inserting an electroporator head fitted with a matrix electrode into the mixture of the spores and the RNA, and energizing, to generate an electric field inside the mixture of the spores and the RNA. The cell culture plate was placed on the ice bath again for 10 min after electroporation, and subsequently the mixture of the spores and the RNA was aspirated off, to obtain resting spores of *Aspergillus niger* with introduction of exogenous RNA.

In this example, the parameters for electroporation include: a voltage of 400 V, pulse duration of 2000 ms, and repeat for 3 times a tan interval of 500 ms.

4) Confirmatory Experiment

The aspirated mixture of the spores and the RNA was added to a 100 volumes YPD medium and cultured at a temperature of 30° C. for 20 hours. Then it was observed by a laser confocal microscope.

At the same time when the above experimental steps were performed, a control was prepared. The same mixture of "the spores and the RNA" that was not electroporated was added to a 100 volumes YPD medium and cultured at a temperature of 30° C. for 20 hours. Then it was observed by a laser confocal microscope too.

Figure 2:
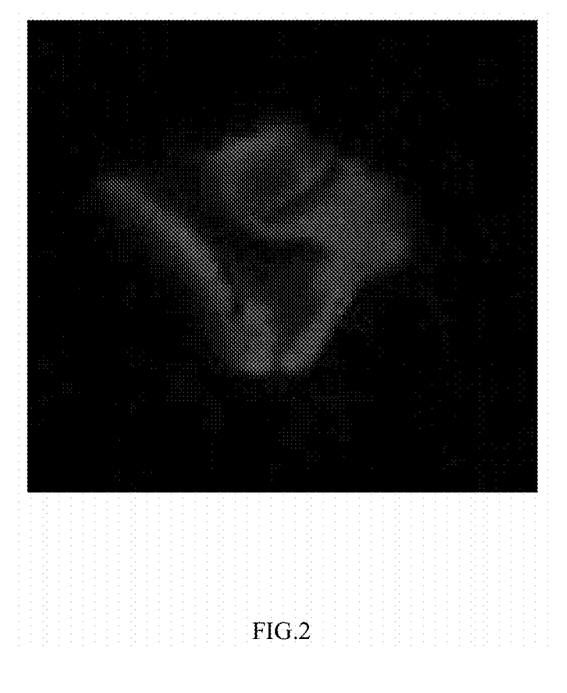
FIG. 2 is fungi with green fluorescence taken by confocal microscope in Example 1.

The results showed that cells in the control had no fluorescence, and at least 95% cells in the sample group had green fluorescence, indicating successful RNA transformation, which was shown in FIG. 2.

Example 2

Expression of Red Fluorescent Protein (RFP) in *Aspergillus niger* Cells:

1. Construction of Plasmid for In Vitro Transcription

The RFP gene encoding sequence is shown in SEQ ID No. 7,

The RFP protein sequence is shown in SEQ ID No. 8,

PCR primers for amplification of RFP gene:

RFP-F:
5' CGGAATTC<u>GCCACC</u>ATGGCCTCCTCCGAGGACGT 3',
with EcoR I site.

RFP-R:
5' TCGAGCTCGTTAGGCGCCGGTGGAGTGG 3',
with Sal I site.

In RFP-F, the <u>GCCACC</u> sequence near the 5' end is used to promote binding of eukaryotic translation initiation factor and RNA which in vitro transcribed from DNA, this sequence adjacent to the target gene's start codon ATG.

RFP-R' 5' end contains Sal I site.

In accordance with example 1, the RFP gene is amplified by PCR, ligated to the PGEM-T easy plasmid, then in vitro transcription, and the resulting RNA will be transformed into the host spores.

2. Using the above-mentioned red fluorescent protein encoded RNA to express red fluorescent protein in *Aspergillus niger* dormant spores, the steps are as follows:

1) Culture of *Aspergillus niger* and Collection of Spores

In a 15-cm Petri dish, a solid agar medium (PDA medium) was prepared.

*Aspergillus niger* CBS 513.88 was inoculated onto the surface of the solid agar medium and cultured at a temperature of 16° C. with 15-50% humidity for 15 days, to allow *Aspergillus niger* spores to overgrow on the surface of the medium (where the spores appeared dark brown and was easy to visually identified).

Sterilized water was poured onto the surface of the medium, to wash down the *Aspergillus niger* spores off from the surface of the medium (by vibrating, or gently scratching with a sterilized smooth glass spreading rod). The spore suspension was aspirated with a pipette and filtered using sterilized lens paper (or fritted glass filter, filter paper, etc.) to remove the mycelia and retain the spores. The filtered liquid was placed in a centrifuge tube and centrifuged to collect the pelleted resting spores, and the supernatant was discarded. The collected spores were subjected to chromosome staining, to observe and confirm that the chromosomes in the spores are haploid.

2) Pretreatment of *Aspergillus niger* Spores

The spore pellets were re-suspended in an electroporation buffer (where the volume of the electroporation buffer added should fill up the centrifuge tube), centrifuged again to collect the spore pellets, and the supernatant was discarded. After repeating the above steps twice, the spores were re-suspended in the electroporation buffer again, and observed under a microscope, to confirm that the spore suspension was free of contamination with mycelia and the spores were non-germinated. When the spores were finally re-suspended in the electroporation buffer, the volume of the electroporation buffer was controlled to maintain a spore concentration in the *Aspergillus niger* spore suspension of $10^{11}$ spores/ml.

The electroporation buffer consisted of HEPES having a final concentration of 0.01 mmol/L and mannitol having a final concentration of 0.5 mmol/L, and the pH of the electroporation buffer was 3.0.

3) Electroporation of the *Aspergillus niger* Spores by Using HDEN Method 0.6 µl of the *Aspergillus niger* spores suspension and 0.1 µg of GFP protein encoding RNA were added to wells of a 96-well cell culture plate and mixed evenly, to obtain a mixture of the spores and RNA. The cell culture plate was placed on an ice bath for 15 min, electroporation was carried out subsequently by using the HDEN method using an Etta Biotech X-Porator H1 electroporator, by inserting an electroporator head fitted with a matrix electrode into the mixture of the spores and the RNA, and energizing, to generate an electric field inside the mixture of the spores and the RNA. The cell culture plate was placed on the ice bath again for 15 min after electroporation, and subsequently the mixture of the spores and the RNA was aspirated off, to obtain resting spores of *Aspergillus niger* with introduction of exogenous RNA.

In this example, the parameters for electroporation include: a voltage of 1 V, pulse duration of 2000000 ms, and repeat for 100 times at an interval of 5 ms.

4) Confirmatory Experiment

The aspirated mixture of the spores and the RNA was added to a 10 volumes YPD medium and cultured at a temperature of 10° C. for 25 hours. Then it was observed by a laser confocal microscope.

At the same time when the above experimental steps were performed, a control was prepared. The same mixture of "the spores and the RNA" that was not electroporated was added to a 10 volumes YPD medium and cultured at a temperature of 10° C. for 25 hours. Then it was observed by a laser confocal microscope too.

Figure 3:
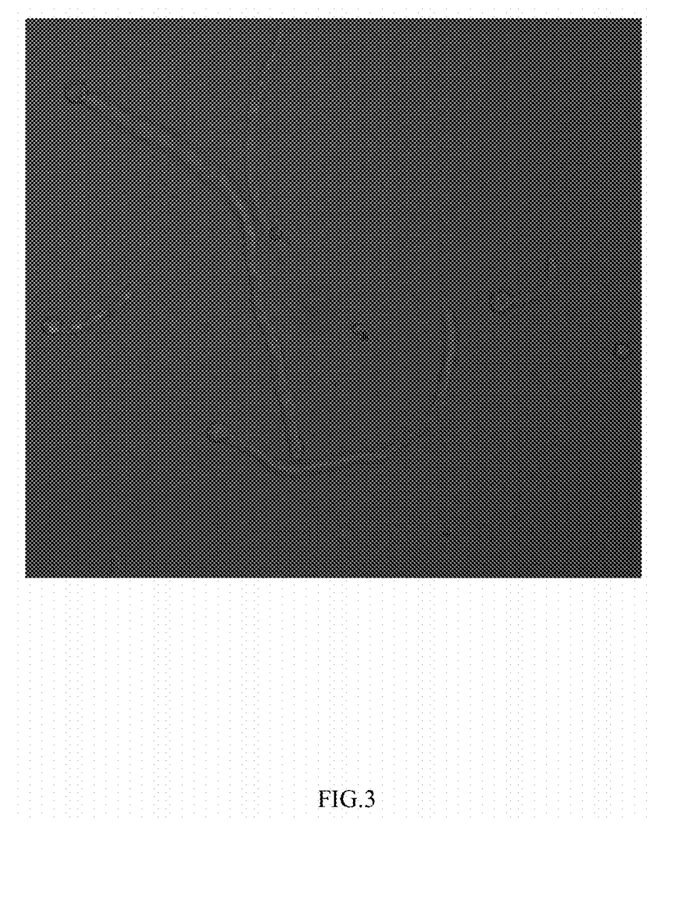
FIG. 3 is fungi with red fluorescence taken by confocal microscope in Example 2.

The results showed that cells in the control had no fluorescence, and at least 90% cells in the sample group had red fluorescence, indicating successful RNA transformation, which was shown in FIG. 3.

Example 3

Expression of yellow fluorescent protein (YFP) in *Aspergillus niger* cells:

1. Construction of Plasmid for In Vitro Transcription

The YFP gene encoding sequence is shown in SEQ ID No. 9,

The YFP protein sequence is shown in SEQ ID No. 10,

In accordance with example 1, the YFP gene is amplified by PCR using the same primers as GFP, ligated to the PGEM-T easy plasmid, then in vitro transcription, and the resulting RNA will be transformed into the host spores.

2. Using the above-mentioned yellow fluorescent protein encoded RNA to express yellow fluorescent protein in *Aspergillus niger* dormant spores, the steps are as follows:

1) Culture of *Aspergillus niger* and Collection of Spores

In a 15-cm Petri dish, a solid agar medium (PDA medium) was prepared.

*Aspergillus niger* CBS 513.88 was inoculated onto the surface of the solid agar medium and cultured at a temperature of 40° C. with 60-85% humidity for 3 days, to allow *Aspergillus niger* spores to overgrow on the surface of the medium (where the spores appeared dark brown and was easy to visually identified).

Sterilized water was poured onto the surface of the medium, to wash down the *Aspergillus niger* spores off from the surface of the medium (by vibrating, or gently scratching with a sterilized smooth glass spreading rod). The spore suspension was aspirated with a pipette and filtered using sterilized lens paper (or fritted glass filter, filter paper, etc.) to remove the mycelia and retain the spores. The filtered liquid was placed in a centrifuge tube and centrifuged to collect the pelleted resting spores, and the supernatant was discarded. The collected spores were subjected to chromosome staining, to observe and confirm that the chromosomes in the spores are haploid.

2) Pretreatment of *Aspergillus niger* Spores

The spore pellets were re-suspended in an electroporation buffer (where the volume of the electroporation buffer added should fill up the centrifuge tube), centrifuged again to collect the spore pellets, and the supernatant was discarded. After repeating the above steps twice, the spores were re-suspended in the electroporation buffer again, and observed under a microscope, to confirm that the spore suspension was free of contamination with mycelia and the spores were non-germinated. When the spores were finally re-suspended in the electroporation buffer, the volume of the electroporation buffer was controlled to maintain a spore concentration in the *Aspergillus niger* spore suspension of $10^4$ spores/ml.

The electroporation buffer consisted of HEPES having a final concentration of 100 mmol/L and mannitol having a final concentration of 5000 mmol/L, and the pH of the electroporation buffer was 7.0.

3) Electroporation of the *Aspergillus niger* Spores by Using HDEN Method

600000 μl of the *Aspergillus niger* spores suspension and 10000 μg of YFP protein encoding RNA were added to wells of a 96-well cell culture plate and mixed evenly, to obtain a mixture of the spores and RNA. The cell culture plate was placed on an ice bath for 10 min, electroporation was carried out subsequently by using the HDEN method using an Etta Biotech X-Porator H1 electroporator, by inserting an electroporator head fitted with a matrix electrode into the mixture of the spores and the RNA, and energizing, to generate an electric field inside the mixture of the spores and the RNA. The cell culture plate was placed on the ice bath again for 10 min after electroporation, and subsequently the mixture of the spores and the RNA was aspirated off, to obtain resting spores of *Aspergillus niger* with introduction of exogenous RNA.

In this example, the parameters for electroporation include: a voltage of 6000 V, pulse duration of 2 ms, and repeat for 1 times at an interval of 50000 ms.

4) Confirmatory Experiment

The aspirated mixture of the spores and the RNA was added to a 10 volumes YPD medium and cultured at a temperature of 40° C. for 24 hours. Then it was observed by a laser confocal microscope.

At the same time when the above experimental steps were performed, a control was prepared. The same mixture of "the spores and the RNA" that was not electroporated was added to a 10 volumes YPD medium and cultured at a temperature of 40° C. for 24 hours. Then it was observed by a laser confocal microscope too.

Figure 4:
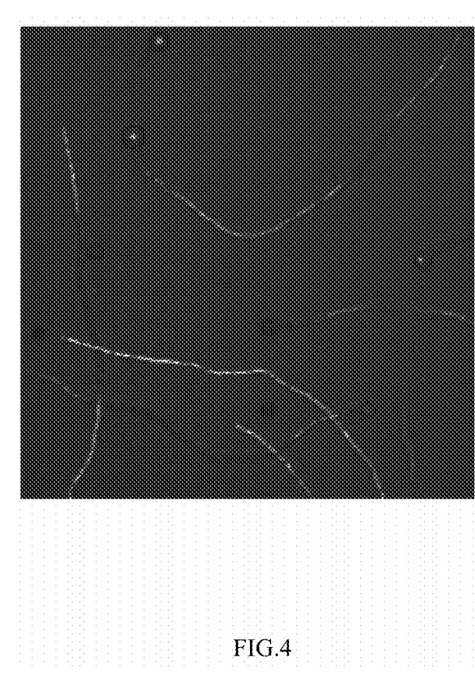
FIG. 4 is fungi with yellow fluorescence taken by confocal microscope in Example 3.

The results showed that cells in the control had no fluorescence, and at least 90% cells in the sample group had yellow fluorescence, indicating successful RNA transformation, which was shown in FIG. 4.

Example 4

In this example, the parameters for electroporation include: a voltage of 30 V, pulse duration of 1000000 ms, and repeat for 50 times at an interval of 5000 ms. The remaining steps are the same as example 1.

Example 5

In this example, the parameters for electroporation include: a voltage of 3000 V, pulse duration of 100 ms, and repeat for 5 times at an interval of 25000 ms. The remaining steps are the same as example 1.

The single-stranded RNA coding protein mentioned in this invention can be the natural protein which is constitutive expression in the host, as well as protein of another species, and novo artificial designed protein.

All protein coding single-stranded RNA can be transformed by the method of the present invention, not be restricted to the embodiment of the green, red or yellow fluorescent protein encoding RNA.

I claim:

1. A method for direct transformation of exogenous single-stranded RNA into resting spores of *Aspergillus niger* to express protein, comprising the steps of:

A) culturing *Aspergillus niger* and collecting spores, as follows:
   inoculating *Aspergillus niger* onto a surface of a solid agar medium, and culturing until *Aspergillus niger* spores are overgrown on the surface of the medium, washing the *Aspergillus niger* spores from the surface of the medium to create a suspension of spores, aspirating off and filtering the suspension of the spores to remove mycelia, collecting the filtrate containing the spores, and centrifuging the filtrate to collect pelleted resting spores;

B) pretreating the *Aspergillus niger* spores, as follows:
   re-suspending the spores in an electroporation buffer, and centrifuging to collect spore pellets, repeating the re-suspension and centrifugation steps 3-4 times, and re-suspending the last collected spore pellets in the electroporation buffer, to obtain an *Aspergillus niger* spore suspension with a spore concentration of $10^4$-$10^{11}$ spores/ml,
   wherein the electroporation buffer consists of 4-hydroxyethyl piperazineethanesulfonic acid having a final concentration of 0.01-100 mmol/L and mannitol having a final concentration of 0.5-5000 mmol/L, and the pH of the electroporation buffer is 3.0-9.5; and C) electroporating the *Aspergillus niger* spores by using high-density distributed electrode network (HDEN) method, as follows:
   adding the *Aspergillus niger* spore suspension prepared in step B) and a RNA to be transformed to wells of a cell culture plate and mixing uniformly, to obtain a mixture of the spores and the RNA, placing the cell culture plate on an ice bath for 10-15 min, subsequently electroporating using the HDEN method, by inserting an electroporator head fitted with a matrix electrode into the mixture of the spores and the RNA, and energizing, to generate an electric field inside the mixture of the spores and the RNA, placing the cell culture plate on the ice bath again for 10-15 min after electroporation, and subsequently aspirating off the mixture of the spores and the RNA, to obtain resting spores of *Aspergillus niger* with introduction of exogenous RNA, wherein a ratio of the *Aspergillus niger* spore suspension to the RNA to be transformed is 0.6-60000 μl of *Aspergillus niger* spore suspension to 0.1-10000 μg of RNA;

wherein parameters for the electroporation comprise: a voltage of 1-6000 V, pulse duration of 2-2000000 ms, and repeat for 1-100 times at an interval of 5-50000 ms;

the RNA to be transformed is a single-stranded RNA encoding an exogenous protein; and the RNA encodes green fluorescent protein, red fluorescent protein, or yellow fluorescent protein.

2. The method for direct transformation of exogenous single-stranded RNA into resting spores of *Aspergillus niger* to express protein according to claim 1, wherein, the medium in the step A) is potato dextrose agar (PDA) medium, yeast extract-peptone-dextrose (YPD) medium, or Czapek-Dox medium.

3. The method for direct transformation of exogenous single-stranded RNA into resting spores of *Aspergillus niger* to express protein according to claim 1, wherein, in the step A), *Aspergillus niger* is cultured at a temperature of 16-40° C. with 15-85% humidity for 3-15 days.

4. The method for direct transformation of exogenous single-stranded RNA into resting spores of *Aspergillus niger* to express protein according to claim 1, wherein, in the step B), the *Aspergillus niger* spore suspension is observed under a microscope before electroporation, to confirm that the spore suspension is free of contamination with mycelia and the resting spores are non-germinated, and subsequently carrying out the electroporation.

5. The method for direct transformation of exogenous single-stranded RNA into resting spores of *Aspergillus niger* to express protein according to claim 1, wherein, in the step C), in which the ratio of the *Aspergillus niger* spore suspension to the RNA to be transformed is 60 μl of *Aspergillus niger* spore suspension to 10 μg of RNA to be transformed.

6. The method for direct transformation of exogenous single-stranded RNA into resting spores of *Aspergillus niger* to express protein according to claim 1, wherein, in the step C), the parameters for the electroporation comprise: a voltage of 400 V, pulse duration of 2000 ms, and repeat for 3 times at an interval of 500 ms.

* * * * *